United States Patent [19]

Wunderlich et al.

[11] Patent Number: 5,578,307
[45] Date of Patent: Nov. 26, 1996

[54] SHAPED ARTICLES CONTAINING PLANT EXTRACT(S), IN PARTICULAR PELLETS, AND THEIR PHARMACEUTICAL OR COSMETIC USE

[75] Inventors: Jens-Christian Wunderlich, Heidelberg; Ursula Schick, Schriesheim; Jürgen Werry, Ludwigshafen; Jürgen Freidenreich, Schriesheim, all of Germany

[73] Assignee: Alfatec-Pharma GmbH, Heidelberg, Germany

[21] Appl. No.: 256,651

[22] PCT Filed: Jan. 18, 1993

[86] PCT No.: PCT/DE93/00037

§ 371 Date: Oct. 18, 1994

§ 102(e) Date: Oct. 18, 1994

[87] PCT Pub. No.: WO93/13754

PCT Pub. Date: Jul. 22, 1993

[30] Foreign Application Priority Data

Jan. 17, 1992 [DE] Germany ............... 42 01 172.8
Jan. 17, 1992 [DE] Germany ............... 42 01 179.5

[51] Int. Cl.$^6$ .................. A61K 35/78; A61K 9/127; A61K 9/64; A61K 9/14
[52] U.S. Cl. ............. 424/195.1; 424/451; 424/456; 424/464; 424/484; 424/485; 424/486; 424/487; 424/488; 424/492; 424/520
[58] Field of Search ............... 424/195.1, 451, 424/456, 464, 484, 485, 486, 487, 488, 492, 520

[56] References Cited

FOREIGN PATENT DOCUMENTS

| 770604 | 12/1971 | Belgium | A61K 31/68 |
|---|---|---|---|
| 1259081 | 3/1961 | France . | |
| 1397583 | 3/1965 | France | A61K 9/50 |
| 454386 | 1/1928 | Germany | A61K 9/16 |
| 242323 | 12/1925 | United Kingdom | A61K 9/16 |

OTHER PUBLICATIONS

Chem Abstrs. 1/3(13):1/4127d, 1990.

*Primary Examiner*—John W. Rollins
*Attorney, Agent, or Firm*—Burns, Doane, Swecker & Mathis

[57] ABSTRACT

Shaped articles containing plant extract(s), in particular pellets, are formed by dispersing the plant extract(s) in a matrix predominantly composed of a skeleton builder, i.e. collagen, gelatin, fractionated gelatin, a collagen hydrolysate, a gelatin derivative, plant protein or plant protein hydrolysate. They are storage-stable, and their pharmacological and cosmetic characteristics are essentially unaltered in comparison with the native extract. They are prepared by a simple process in which liquid plant extract(s) is(are) mixed or emulsified in a solution of the skeleton builder, or solid extracts are dissolved or suspended in a solution of the skeleton builder, the dispersion of skeleton builder and plant extract(s) is added dropwise to an intensely cold, inert, liquefied gas, preferably liquid nitrogen, thus shaping the pellets, and the shaped pellets are dried. The plant extract employed is preferably Aloe vera juice.

37 Claims, No Drawings

SHAPED ARTICLES CONTAINING PLANT EXTRACT(S), IN PARTICULAR PELLETS, AND THEIR PHARMACEUTICAL OR COSMETIC USE

The present invention relates to pellets or true spheres containing plant extract(s) and which comprise a dispersion of the plant extract in a matrix predominantly composed of a skeleton builder of a hydrophilic macromolecule.

The invention furthermore relates to a mild process for the preparation of such pellets or true spheres and to their pharmaceutical, peroral or cosmetic application.

The plant extract which is preferably employed is Aloe vera juice.

The plant extracts in the sense of the present invention are juices from fresh plants obtained directly from the plant, pressed-out juices from fresh plants, either in the original concentration or in concentrated form, filtered and unfiltered, hydrophilic extracts (aqueous or alcoholic extracts, for example ethanol extracts or 1,2-propylene glycol extracts) such as, for example, original tinctures in homeopathy, fluid extracts, macerates, lipophilic extracts (such as, for example, garlic oil), essential oils, complete extracts or specifically standardized extracts (for example standardized to a specific flavone glycoside content), essential oil extracts, individually isolated plant constituents (such as, for example, rutin), synthetic analogs (such as, for example, perfume oils, camphor, thymol, vanillin) and derivatized plant constituents (such as, for example, aglycones).

In individual cases, it is also possible to use dry extracts or the redissolved extract from a dry extract in a suitable solvent, or decoctions prepared therefrom. Pulverized drug constituents (for example leaves, roots, herbaceous parts) can also be processed.

Being natural substances, plant extracts are frequently sensitive to external factors such as light, oxidation by atmospheric oxygen, heat, pH effects in solutions, or microbial contamination. In many plant-derived active substances, it is known that only the fresh juice obtained originally from the plant or parts thereof (for example Echinacea pressed-out juice or Aloe vera juice) have optimum activity. Each means of preservation, such as drying by heat, chemical preservation, heat treatment for preservation purposes and the like adversely affect the delicate plant constituents with regard to their chemical structure and thus their activity. In most cases, preservation against microbial contamination is unavoidable when using fresh plant juices so as to achieve at least limited shelf life.

In addition, the dry matter content of such fresh plant juices is very low, and a large amount of water is being transported or stored.

Lipophilic plant extracts which are sensitive to oxidation, such as vitamin E or garlic oil, are difficult to store in unaltered form and usually have to be processed at once.

Essential oils are volatile and difficult to handle in the form of liquids.

Aloe vera (Aloe barbadensis Miller; synonyms: Aloe vera Tournefort et Linné, Aloe vulgaris Lamarck) has been used for a long time in traditional medicine of those regions in which this plant, which belongs to the family of the Liliaceae grows wild.

If used externally, the gel-like plant juice has, for example, a beneficial effect on wound healing, acts as an antibiotic or has a softening effect on the skin.

Aloe vera juice can be administered internally in the treatment of gastric diseases and disorders of the gastrointestinal tract. Anti-inflammatory properties have also been reported.

These original findings have led to large plantations of Aloe vera having been established in Central America, South America and parts of North America. The juice in the leaves is obtained at the site itself in a laborious process and subsequently concentrated under the mildest possible conditions. The concentration of plant constituents in the freshly obtained juice is between 0.3 and approximately 1%. Fresh Aloe vera fillets, aqueous concentrates or spray- or freeze-dried goods are all commercially available. The differences in quality of commercially available products are considerable with regard to stability and composition and depend largely on the preparation technology employed.

Aqueous concentrates or the juice from the leaves are currently being used successfully in dermatoses (for example burns by the action of heat, UV rays or X-rays), chemical burns, wounds, gastric diseases or parodontosis. It appears that the pharmacological effect is only to be attributed to the total of all constituents. A demonstration of the effect of individual components is currently being investigated extensively.

However, since no undesired side-effects of Aloe vera juice are known, this natural product has been offered for sale for many years in creams, moisturizing emulsions, sun care products or for internal use.

The shelf life, or stability of storage, of the aqueous plant gel causes substantial difficulties. Despite preservation, the liquid product is unstable to the action of heat and pH, sensitive to oxygen and, moreover, highly susceptible to microbial contamination.

The transport of fresh Aloe vera juice is difficult and costly due to the high liquid volume—90–99% of water are transported—and the abovementioned instability phenomena. Moreover, the juice must be cooled until it is used in production. The preparation methods which involve the process steps initial washing of the leaves, obtaining the fillets, homogenization, purification and filtration, concentration and drying, can result in changes in the constituents and bacterial contamination of the end product in question if the technology used is unsuitable.

Aloe vera powders obtained by spray- or freeze-drying are only sparingly redissolvable in cold water since they lack wettability and because there is a danger of lump formation. Moreover, freeze-dried products are hygroscopic and easily form lumps when stored inadequately. Commercially available products which are readily dissolvable in water are frequently treated with surfactants, which are undesired in cosmetics.

It is therefore an object of the invention to provide unpreserved, storage-stable, concentrated, solid or semi-solid forms of plant extracts, in particular of Aloe vera juice, which can be redissolved without problem and whose pharmacological and cosmetic properties remain unaltered compared with the native plant juice.

This object is achieved according to the invention by pellets containing plant extract, which comprise a dispersion of the plant extract in a matrix containing predominantly a skeleton builder of a hydrophilic macromolecule.

The following are employed as hydrophilic macromolecules: collagen, gelatin, fractionated gelatin, collagen hydrolysates, gelatin derivatives, plant proteins, plant protein hydrolysates, elastin hydrolysates; and mixtures of the abovementioned substances.

This object is furthermore achieved by a process for the preparation of pellets containing plant extract(s), which comprises mixing or emulsifying the skeleton builder in solid or dissolved form with liquid plant extract, or dissolving or suspending solid extracts in a solution of the skeleton builder and making the product into shaped articles. If required, the shaped articles can be dried. The only aspect that requires attention is that matrix systems and active substance must not be incompatible.

In particular, the present invention provides shaped articles containing a plant extract, which comprise a dispersion of the plant extract in a matrix composed predominantly of a skeleton builder of hydrophilic macromolecules selected from the group consisting of: collagen, gelatin, fractionated gelatin, collagen hydrolysates, gelatin derivatives, elastin hydrolysates, plant proteins, plant protein hydrolysates; and their mixtures.

The present invention furthermore provides a process for the preparation of shaped articles containing plant extract, wherein a) a skeleton builder of hydrophilic macromolecules selected from the group consisting of: collagen, gelatin, fractionated gelatin, collagen hydrolysates, gelatin derivatives, plant proteins, plant protein hydrolysates, elastin hydrolysates; and their mixtures, is mixed with plant extracts selected from the group consisting of:

hydrophilic liquid plant extracts, aqueous extracts, alcoholic extracts; and their mixtures; and b) the resulting mixture of skeleton builder and plant extract is added dropwise to an intensely cold inert liquid, thus making it into shaped articles.

Preferred embodiments of the invention are described and claimed in the subclaims.

The following are examples of plant extracts or of extracts or individual substances obtained therefrom: Flavonoids and their aglycones: rutin, quercetin, diosmin, hyperoside, (neo-)hesperidin, hesperitin, Ginkgo biloba (for example ginkgo flavone glycosides), Crataegus extract (for example oligomeric procyanidines), buckwheat (for example rutin), Sophora japonica (for example rutin), birch leaves (for example quercetin glycosides, hyperoside and rutin), elderflower (for example rutin), lime flower (for example essential oil containing quercetin and farnesol), St John's wort oil (for example olive oil extract), calendula, arnica (for example oily extracts of the flowers with essential oil, polar extracts with flavonoids), balm (for example flavones, essential oil), Essential oils: sage (for example essential oil containing thymol), aniseed (for example essential oil containing transanethol), oil of cloves (for example essential oil containing eugenol), camomile (for example chamazulene, alpha-bisabolol), myrtol: (limonene, alpha-pinene, cineol), oil of peppermint (for example oil containing menthol), caraway (for example oil containing carvone), dwarf pine oil (for example oil containing alpha-pinene), juniper, rosemary, eucalyptus oil, lavender, fir leaf oil, bergamot oil, citrus oil, balm, marjoram, thyme, basil (stomachic tonics or condiments), fennel Fatty oils: for example wheatgerm oil and vitamin E isolated therefrom, oil of evening primrose (for example gammalinolenic acid), plant lecithins (for example soybean lecithin), sphingolipids/ceramides isolated from plants Immunostimulants: Echinacea purpurea (for example alcoholic extracts, fresh plant juice, pressed-out juice), Eleutherococcus senticosus Alkaloids: rauwolfia (for example prajmalin), periwinkle (for example vincamin)

Other phytopharmaceuticals: aloe, horse chestnut (for example aescin), garlic (for example garlic oil), pineapple (for example bromelains), ginseng (for example ginsenosides), Our Lady's thistle fruit (for example extract standardized with regard to silymarin), box holly root (for example ruscogenin), valerian (for example valepotriates, Tct. Valerianae), kava kava (for example kavalactones), hop flowers (for example hop bitters), Extr. Passiflorae, gentian (for example ethanolic extract), anthraquinone-containing drug extracts, for example aloin-containing Aloe vera juice, pollen extract, extracts from algae, licorice extracts, palm extract, galphimia (for example original tincture), mistletoe (for example aqueous ethanolic extract), phytosterols (for example beta-sitosterin), verbascum (for example aqueous-alcoholic extract), drosera (for example vinum liquorosum extract), sea buckthorn fruit (for example juice obtained therefrom or sea buckthorn oil), marshmallow root, primula root extract, fresh plant extracts of mallow, comfrey, ivy, horsetail, yarrow, ribwort (for example pressed-out juice), stinging nettle, greater celandine, parsley.

Plant extracts of Norolaena lobata, Tagetes lucida, Tecoma siems, Momordica charantia.

As a rule, the plant extract is generally selected from the group consisting of: solid plant extracts, liquid plant extracts, hydrophilic plant extracts, lipophilic plant extracts, individual plant constituents; and mixtures of these.

In general, the literature mentions Aloe vera juice, Aloe vera gel and Aloe vera extracts. The term "Aloe vera juice" used in the sense of the invention is to be understood as meaning, in general, the native juice obtained directly from the leaf, the filtered or purified juice, the juice which has been concentrated under mild conditions and also the redissolved juice made of a dry extract. For internal use, it is also possible to use the whole leaf, leaf constituents and flowers in homogenized form. Alternatively, individual constituents may be suitable for specific uses.

The pellets according to the invention are spherical, uniform shaped articles whose diameters have a customary range of 0.8–2 mm. Moreover, sizes of 0.2–0.8 and 2–12 mm can be prepared according to the invention. Pellets with a diameter of over 2 mm are termed true spheres in the present invention, and they are suitable as single unit dosage form.

Surprisingly, the pellets display a great mechanical strength combined with a low degree of abrasion (friability). They are storage-stable, can be metered readily and are obtained as a free-flowing material due to the specific preparation process. They can contain plant extract(s) at concentrations of 0.1–98% (percent by weight), preferably 0.1–60%, calculated as solids.

Surprisingly, neither the nature nor the composition of the constituents of the native plant constituents are altered by the pellets according to the invention. As a cold process, the process according to the invention is a very mild form of processing. The pellets containing plant extract(s) can exist in the form of a lyophilisate or in the form of solid or gel-like pellets, depending on the preparation.

Preservatives or a heat treatment for preservation purposes can be dispensed with by conversion into pellet form, using the matrix systems according to the invention.

A pelleted fresh plant juice is storage-stable. If, for example, solvent extraction is required for stability reasons, this can be dispensed with.

Furthermore, liquids can be converted into the solid form (essential oils or fatty oils). This improves storage stability, transportability and the handling quality of such substances.

The pellets, which have been dried conventionally according to the invention, with or without addition of plasticizers, can be recognized easily by their characteristic, typical appearance: they are transparent or opalescent.

The product according to the invention can be employed directly for pharmaceutical purposes, for internal use or for cosmetic purposes.

For pharmaceutical purposes, the pellets, as multiple unit dosage forms, can be filled into sachets or hard gelatin capsules in the form of granules, furthermore in the form of beverage granules for the preparation of drink solutions (for example instant teas), and they can be packaged as single unit dosage forms, i.e. single unit dose pellets for example filled into suitable containers, blister packs or dosing dispensers for withdrawing them singly. A further single unit form is represented by rapidly dissolving tablets made by compressing freeze-dried pellets.

For cosmetic uses, it is particularly advantageous according to the invention to use plant proteins or hydrolysates thereof, soluble collagen, gelatin, collagen hydrolysates, elastin or elastin hydrolysates as carrier materials of the shaped articles.

Gelatin is a scleroprotein obtained from collagen-containing material, and its properties vary depending on the preparation process. It is composed essentially of four molecular weight fractions which have an effect on physicochemical properties as a function of the molecular weight and the percentage by weight. For example, the more microgel (107 to 108 D) present, the higher the viscosity of the aqueous solution. Commercially available types contain up to 15 percent by weight. The fractions of alpha-gelatin and the oligomers thereof ($9.5 \times 10^4/10^5$ to $10^6$ D) are decisive for the solidity of the gel and they are conventionally between 10 and 40 percent by weight. Molecular weights below those of alpha-gelatin are designated as peptides and can amount to up to 80 percent by weight in conventional gelatin qualities (low Bloom value).

The sol/gel conversion behavior of gelatin, which depends on the molecular composition, is a function of temperature and concentration. The Bloom value is a conventional method for indicating the gelling capacity. Low commercial qualities start at 50 Bloom, types with a high Bloom value have around 300 Bloom.

Fractionated gelatin is a specific type of gelatin and is obtained from conventional gelatin by specific preparation processes, such as, for example, ultrafiltration. The composition can be varied, for example, by removing peptides (MW<$9.5 \times 10^4$ D) or by mixing individual fractions, such as, for example, alphachains, dimeric and trimeric chains or microgel.

Collagen in its native form is water-insoluble. Nowadays, specific preparation processes allow soluble collagen types to be obtained.

Gelatin derivatives are chemically altered gelatins such as, for example, succinylated gelatin, and these are also known as plasma expanders.

Collagen hydrolysate is to be understood as a collagen or gelatin product which has no gelling capacity and which has been obtained by pressure hydrolysis or enzymatically. The molecular weight composition can range between a few hundred D up to below $9.5 \times 10^4$ D, depending on the preparation. Collagen hydrolysates are soluble in cold water.

For external use, these substances of biogenic origin are not only distinguished by being well tolerated by the skin, they can also be incorporated particularly easily into ointments, creams and emulsions. Here, they display their specific property of acting somewhat as emulsifiers and emulsion stabilizers. Thus, for example, the use of substantial amounts of surfactants, which are skin irritants, can be reduced further, which contributes to their tolerance by the skin, a demand which must be met by pharmaceutical preparations, for example for the treatment of wounds, or by modern cosmetics. Gelatin and collagen hydrolysates are pharmaceutically recognized auxiliaries which are also preferably employed in the cosmetics industry.

The plant proteins and the hydrolysates thereof are novel products whose characteristics correspond largely to those of the collagen hydrolysates. They are preferably obtained from wheat and soybeans and have molecular weights of, for example, 200,000–300,000 D or 1000–10,000 D.

If plant proteins, plant protein hydrolysates or collagen hydrolysates (gelatins which are soluble in cold water) or gelatins whose molecular weight distribution has a maximum of some hundred D up to below $10^5$ D are used, the lyophilized carrier material of the shaped articles according to the invention, surprisingly, forms a highly-porous network structure which is mechanically stable.

Elastin hydrolysates are obtained enzymatically from elastin and are composed of a single polypeptide chain with a high proportion of non-polar amino acids. They can be used in lipophilic systems due to their hydrophobic properties. Elastin hydrolysates have a molecular weight of approximately 2000–3000 D and are strongly film-forming on the skin.

Rapid dissolution of the pellet formulae described is advantageous for instant uses such as, for example, instant teas, instant drinks (for example cough mixture), or instant creams without preservatives.

The recognized healing effect of fresh plant juices, for example Aloe vera juice, on internal use (health care) can be improved advantageously by the pellets according to the invention in the form of an instant preparation without preservatives. If, for example, a fresh plant juice is cryopelleted together with a rapidly dissolving matrix, storage-stable pellets are obtained, and these (which are, for example, in sachets) can be dissolved completely within a few seconds in water or fruit juices, milk or other beverages. In addition, complete instant beverages can be advantageously prepared according to the invention which are composed of fresh plant juice, a matrix composition of proteins of biogenic origin (for example collagen hydrolysates, wheat proteins) and natural skeleton builders, fruit juice extract, honey and other natural components. Components of the matrix such as, for example, gelatin, can mask unpleasant flavor, and glycerol and sorbitol can act as sweeteners which are gentle on the teeth.

If the pellets according to the invention are not in lyophilized form, but in solid or semi-solid form, they can be constructed advantageously of sol/gel-forming hydrophilic macromolecules, such as, for example, gelatin or fractionated gelatin, where the maximum of the molecular weight distribution is above $10^5$ D and the consistency is a direct function of the nature and concentration of the addition of plasticizer.

Such pellets which contain plasticizers are outstandingly suitable for converting essential oils into a solid, and therefore readily processable, form.

Semi-solid pellets, in particular, can be incorporated into the matrix in such a manner that they melt or dissolve after application. Advantageous for external use in the field of both pharmaceutics and cosmetics is the gentleness on the skin of the matrix, which is composed of natural substances.

The following text describes the process for the preparation of the pellets according to the invention in greater detail.

More details in this context can be found in the parallel international (PCT) applications listed hereinbelow. The contents of these parallel PCT applications, which were filed at the German Patent Office on the same day by the same inventors and applicants:

Internal file reference: P/81AL2741, title: "Active-substance-containing solid articles having a skeleton of hydrophilic macromolecules, and their preparation", PCT/DE93/

-00038=WO93/13757, priorities claimed: German Patent Application P 42 01 179.5 dated Jan. 1, 1992, German Patent Application P 42 01 173.6 dated Jan. 1, 1992, U.S. Ser. No. 07/876,864 dated Apr. 30, 1992 and U.S. Ser. No. 07/876,877 dated Apr. 30, 1992.

Internal file reference: P/81AL2742, title: "The preparation of soft-gelatin capsules by a dripping process", PCT/DE93/-00035=WO93/13761, priorities claimed: German Patent Application P 42 01 178.7 dated Jan. 1, 1992 and U.S. Ser. No. 07/876,863 dated Apr. 30, 1992.

Internal file reference: P81AL2743, title: "Pellets containing pharmaceutically active peptides, their preparation and their use" PCT/DE93/00036=WO93/13753, priorities claimed: German Patent Application P 42 01 179.5 dated Jan. 17, 1992 and U.S. Ser. No. 07/876,865.

In their entirety are herewith made a disclosure of the present application, as are the earlier PCT applications: PCT/DE92/01010, PCT/DE92/01012, PCT/DE92/01014, PCT/DE92/01016, PCT/DE92/01007, PCT/DE92/0 1008, PCT/DE92/01015, PCT/DE92/01013, PCT/DE92/01009, PCT/DE92/01011 dated Dec. 4, 1992.

If the extract is aqueous, alcoholic or aqueous/alcoholic, the process according to the invention for the preparation of pellets containing plant extract(s) can be described by the following two process steps:

a) A skeleton builder of hydrophilic macromolecules from the group consisting of: collagen, gelatin, fractionated gelatin, collagen hydrolysates, gelatin derivatives, plant proteins, plant protein hydrolysates and elastin hydrolysates, in solid or dissolved form, is mixed with liquid, hydrophilic (aqueous, alcoholic or aqueous/alcoholic) plant extract.

b) The resulting mixture of skeleton builder and liquid hydrophilic plant extract is introduced dropwise into an intensely cold inert liquefied gas, thus making shaped articles.

A shaped article in the sense of the invention is to be understood as one selected from the group consisting of: powders, granules, pellets and essentially symmetric aggregates.

In the description of the invention, characteristics, preparation and use will be illustrated by way of preference with round pellets.

However, a person skilled in the art will also be able to employ other shaped articles from the group consisting of: powders, granules and essentially symmetric aggregates advantageously for the preparation of, in particular, pharmaceutical formulations.

If, for example, collagen hydrolysates or plant protein hydrolysates which are soluble in cold water are employed as skeleton builders, the process can be carried out in the absence of heat, i.e. in the mildest manner possible.

In an embodiment of the process described under a), a composition which is capable of forming drops, preferably composed of hydrophilic macromolecules as skeleton builders, in particular plant proteins, plant protein hydrolysates, collagen, gelatin, fractionated gelatin, collagen hydrolysates, elastin hydrolysates or gelatin derivatives and aqueous, alcoholic or aqueous/alcoholic plant extract is prepared.

First, the desired skeleton builder, in particular plant proteins, plant protein hydrolysates, collagen, gelatin, fractionated gelatin, gelatin derivatives or collagen hydrolysates, are dissolved either in the freshly obtained or in the already concentrated, liquid aqueous, alcoholic or aqueous/alcoholic plant extract, or the skeleton builder is already in dissolved form and as such mixed with the plant extract, type and quantity of the skeleton builder employed and, if appropriate, an addition of other auxiliaries depending on the intended use of the pellets at a later point in time. The concentration of the carrier material can range, for example, from 0.5 to 60% (w/w), preferably 0.5 to 30% (based on the composition to be processed). If gelatin is employed, for example, then heat in a temperature range of 30° C. to 45° C. may have to be used in order to convert the gelatin into the sol form.

Furthermore, additives of the group consisting of: albumin, agar-agar, gum arabic, pectins, tragacanth, xanthan, natural and modified starches, dextrans, dextrins, maltodextrin, chitosan, alginates, cellulose derivatives, polyvinylpyrrolidone, dextran, sugars, glycine, lactose, mannitol, polyacrylic acid, methacrylic acid polymers, methacrylate polymers, and their mixtures may be added at a concentration of 1–50%.

Further auxiliaries and carriers which are suitable for cosmetic, internal or pharmaceutical application, such as, for example, additional skeleton builders, which are described in greater detail further below, plasticizers such as, for example, glycerol or sorbitol, fillers such as, for example, lactose, dispersants such as, for example, disodium phosphate, pH regulators such as, for example, disodium citrate, emulsifiers such as, for example, lecithin, stabilizers such as, for example, ascorbic acid, cosolvents such as, for example, polyethylene glycol, natural colorants such as, for example, carotenoids, flavorings or masking flavors such as, for example, fruit juice concentrates, may be added to this basic matrix.

In a further process variant, 1–50% (based on the composition to be processed) of plasticizers selected from the group consisting of: glycerol, propylene glycol, polyethylene glycols, triacetin, sorbitol, sorbitan mixtures, sorbitol solutions, glucose syrup and other polyols or sugar alcohols, and their mixtures may be added to the matrix.

Furthermore, it may be advantageous from the technological point of view to add other skeleton-building substances to the formula in addition to the skeleton builder of hydrophilic macromolecules.

Additional skeleton builders which can be employed are: albumins, agar-agar, gum arabic, pectins, tragacanth, xanthan, natural and modified starches, dextrans, dextrins, maltodextrin, chitosan, alginates, cellulose derivatives, sugars, such as, for example, sucrose, glycine, lactose, PVP (polyvinylpyrrolidone), mannitol and combinations of the abovementioned substances, but in particular mannitol.

In the case of plant extracts which are exceedingly thermolabile, a further embodiment of the invention surprisingly allows shaped articles to be provided which have the characteristics according to the invention and which have been prepared exclusively under cold conditions. In this procedure, a matrix of a hydrophilic macromolecule is used which is selected from the group consisting of: plant proteins, plant protein hydrolysates, elastin hydrolysates, collagen hydrolysates, gelatin which is soluble in cold water, gelatin derivatives; and mixtures of the abovementioned substances, whose molecular weight distribution has a maximum of below $10^5$ D.

In an embodiment of the invention, additive substances may be selected from this group so as to adapt the physical or chemical properties of the matrix such as, for example, the viscosity, the mechanical strength or the dissolution characteristics of the polymeric skeleton to suit the intended use. Additions of dextrans, modified starches, sugars and, in particular, mannitol, allow, for example, pellets to be prepared according to the invention which dissolve in cold water spontaneously and completely.

Particularly suitable as additions of plasticizers are substances such as, for example, sorbitol, which are solid at room temperature after drying. Surprisingly, the matrix of such pellets forms a solid to semi-solid structure after lyophilization which, when brought into contact with aqueous medium or under physiological conditions, gives a bioadhesive and highly viscous characteristic in the sense of the invention.

If solids, for example dry extracts, are processed, then they can be either dissolved in the liquid matrix or suspended therein.

If liquid, lipophilic extracts (fatty or essential oils) are processed, then they are emulsified in the liquid matrix. The surfactant properties of the matrix constituents, such as, for example, gelatin or collagen hydrolysate, can be utilized in an advantageous manner, so that, in many cases, the process can be carried out without an addition of an emulsifier. This is a considerable advantage when the product is administered perorally, but also when it is used on sensitive or injured skin or in cosmetics. Microemulsions mixed with the matrix may also be pelleted.

Fatty or essential oils which have been encapsulated by simple or complex coacervation and essential oils which have been encapsulated by spray-drying processes can be processed in the matrix according to the invention. It is also possible to produce microcapsules or coacervates in the dissolved matrix itself, and these microcapsules or coacervates together with the matrix are then made into pellets which contain microcapsules incorporated in the matrix. The same applies to nano-capsules.

For cosmetic purposes, it may furthermore be desired to add lipophilic components, such as, for example, phospholipids, to the matrices described so as to form liposomes.

In exceptional cases, the plant constituents themselves, in particular after concentration, may act as skeleton builders for the preparation of pellets according to the invention.

Of course, the mixtures according to the invention are suitable for immediate decanting in liquid form by the process step as described under a) to form containers, such as, for example, moldings, soft-gelatin capsules and other suitable shells.

In an embodiment of the process step described under b), the matrix described is immersed into a bath in the range of −108° C. to −210° C. for rounding off (shaping) and shock frosting. The intensely cold and inert liquid used is preferably liquid nitrogen, which does not alter the constituents of the pellets. Round shaped articles (pellets) are formed in the intensely cold liquid, and these form a mechanically stable matrix after drying. Shaping is effected by a suitable dosing system. Each discrete drop assumes the shape of a sphere, on the one hand as early as during the free descent, on the other hand in the immersion bath due to the gas layer which forms around it or the surface tension between system and gas, whereupon freezing is completed. It is precisely this rapid, but yet controllable freezing which fixes the given state of the system immediately, i.e. no plant extract constituents can diffuse into the surrounding medium, dissolved components can no longer crystallize, suspensions can no longer sediment, emulsions cannot break, plant juice components which are sensitive to high temperatures or moisture are cryopreserved, the carrier skeleton cannot shrink and the like. The preparation process in which an inert liquid gas is used therefore results in no adverse effects or alteration of the product. Preservation of the desired characteristics is therefore particularly advantageous. Moreover, the process is carried out in the absence of solvents, does not pollute the environment and can be carried out under sterile conditions.

Suitable dosing systems are all devices which are capable of producing discrete, uniform drops whose size can be predetermined, for example pipette-like dripping devices, or suitable spray or atomizing nozzles equipped with dosing pumps.

Other devices which can be used for the process according to the invention are dosing devices equipped with single-substance nozzles which expel the material to be made into drops in a pulsed or intermittent fashion.

Another preferred embodiment of the process according to the invention employs the "Cryopel" process (based on DE-OS 37 11 169) developed by Messer Griesheim GmbH. With regard to the equipment used, scaling-up of the process according to the invention to an industrial scale is particularly simple in connection with an immersion frosting plant, the CryopelR plant. This plant, which can be operated with liquid nitrogen, is particularly distinguished by its economy. This plant is also suitable for working under sterile conditions. A continuous operation which requires little maintenance and cleaning allows an economical scaling-up of the process according to the invention to an industrial scale.

FIG. 1 shows a diagram of the CryopelR process developed by Messer Griesheim GmbH. From the heatable feeding device 1, the plant extract/matrix composition according to the invention is added dropwise through metered nozzles into the liquid nitrogen bath 3 at −196° C. where it is made into round pellets while simultaneously being subjected to shock frosting. The frozen product is discharged via device 5 by means of the continuously operating conveyor belt 2. The liquid nitrogen is metered via inlet pipe 7, and the nitrogen gas formed escapes via pipe 6. The entire system is enclosed by the insulation 4.

FIG. 2 shows a diagram of a process in which the plant extract/matrix composition, which is either cold or heated at not more than 50° C., is added dropwise continuously via a controllable dosing pump 8 through the inlet pipe 9 and the heatable dropping nozzle 10 into the insulation trough 11, which contains liquid nitrogen 12. The shock-frosted pellets are withdrawn batchwise. This device allows highly viscous compositions to be processed.

If the system to be processed is not sufficiently flowable or not sufficiently capable of forming drops, another 1–10% by weight of water can be added, for example, or the processing temperature can be raised, or else pressure may be used for the dosing operation. Analogously, a subatmospheric pressure is to be applied in the opposite case (if the viscosity of the system is too low). In this manner, a uniform formation as well as tearing off of the individual droplets are guaranteed.

The processing temperature can vary within wide limits, but should be below 50° C. in the case of specific plant extracts, such as, for example, Aloe vera, to avoid thermal stress of the constituents.

Thus, a Cryopel dosing device allows compositions whose viscosity varies within a wide range, for example $1 \times 10^{-3}$ to 12.5 Pa×s (Pascal seconds) to be dosed in a problem-free manner.

Other intensely cold liquids which are suitable for the process according to the invention may be, for example, liquid rare gases, such as argon.

Depending on the dosing system selected, a particle size uniformity of over 70%, which can additionally be improved by grading, may be achieved.

Fractions removed by grading can be converted back into the liquid state and repelleted, allowing the process to be carried out in a loss-free manner.

In an embodiment of the process step described, the pellets are dried, which results in two process variants.

Variant A:

The pellets, which have been frozen at −196° C., are introduced into a freeze-drying plant. The temperatures selected are from 15° C. below the sublimation point of water at a pressure of 0.1 Pa to 103 Pa (0.001 to 1.03 mbar). The drying process, which proceeds in a conventional freeze-drying plant (condenser temperature −40° C.) at −25° C. and 33 Pa (0.33 mbar) in primary drying with sublimation of the matrix water, which has been frozen in amorphous form by means of shock-frosting, results in an end product having a highly porous network structure after secondary drying (desorption). In comparison with conventionally freeze-dried goods, such pellets are particularly readily soluble and preferably suitable for the development of instant preparations.

Variant B:

The frozen pellets are defrosted and conventionally dried. This process can be carried out advantageously in vacuo (3000–5000 Pa (30–50 mbar)) to accelerate the drying process and to maintain low temperatures. Drying temperatures of up to 50° C. may be selected, the temperature during the drying process in the pellet matrix not rising to above 30° C. due to the evaporation enthalpy of the liquid.

In the case of conventionally dried pellets (variant B), sol/gel-forming substances required for the matrix are those which are capable of forming drops in sol form and which, after cryopelleting or defrosting, form a gel which is stable after drying. An addition of plasticizers has a beneficial effect on the formation of uniformly round shaped articles. Pellets which have been prepared in this manner are distinguished by economical preparation and can be employed both in the cosmetic and the pharmaceutical sector.

Compared with the prior art, the process according to the invention itself can be carried out, on the whole, with a low degree of maintenance and in an economical fashion.

The pellets according to the invention can be suitable for pharmaceutical purposes, but also peroral or cosmetic purposes.

The following are examples of pharmaceutical uses:

Peroral unit dosage form (2–12 mm pellets)

Pellets can also be filled directly into hard-gelatin capsules or sachets.

As a basis for the preparation of tablets, coated tablets and the like.

The pellets are outstandingly suitable for direct tabletting. The high granulometric accuracy which can be achieved means that there are no dosing problems.

Instant teas

In sachets, pellets can be offered for the preparation of health-care drink solutions (instant preparation). If plant proteins, plant protein hydrolysates, collagen hydrolysates or gelatin are used whose molecular weight distribution has a maximum of some hundred D up to below $10^5$ D, the pellets according to the invention dissolve in water at room temperature in the course of a few seconds. Mixtures of a variety of plant extracts or with other active substances are also possible in this form.

The combination of Aloe vera with pharmaceutically active substances, or active substances in dietetics (health care), can furthermore contribute to an improved tolerance of these substances, in particular when administered internally. For example, irritation of the gastric mucosa by acetylsalicylic acid can be reduced effectively by the constituents of the Aloe vera juice, which have a protective action on the mucous membrane.

Balneotherapeutic products, inhalants for dissolution in hot water

Preparation of ointments, creams, gels and the like for the treatment of wounds, for example in the case of burns and chemical burns and the like Preparation of adhesive plasters and powders for use on wounds and the like Pellets of active substance prepared under sterile conditions to be inserted into wounds The following are examples of cosmetic uses:

Preparation of creams, instant creams, moisturizing emulsions, sun care products, products for use against solar dermatitis, shampoos, toothpastes, soaps, bath products, facial toners Direct use of pellets for the preparation of facial masks, powders and the like Use in cosmetics in the dissolved or semi-solid form Use in cosmetics in combination with other active substances Due to the high variability of the formulae and the preparation processes described, the characteristics of the pellets according to the invention can be adjusted in a very simple manner to suit the intended aim.

A specific matrix formation allows direct use of pellets in solid and semi-solid form, dissolution being effected during application.

By varying the Bloom value of the gelatin employed according to the invention it is not only possible to control characteristics such as, for example, the dissolution rate of the pellets according to the invention, but also to adjust a desired viscosity of an aqueous solution of these pellets, again to suit the intended aim.

Such pellets have a series of advantages: the plant constituents remain unaltered in unpreserved form compared with liquid extracts or dry extracts prepared in the customary manner.

If plasticizers are added, they have an inimitable appearance and are, moreover, very acceptable when ingested. Unpleasant flavor is already masked by the matrix components themselves.

They allow an alcohol-free drug preparation for plant extracts to be prepared or they can be employed as homoeopathic globuli. Compared with soft gelatin capsules, the active substance cannot leak. Volatile essential oils are formulated to give a solid preparation. In contrast to commercially available solutions and tinctures, their weight is low, and they can be swallowed easily as unit dosage forms.

The examples which follow are intended to illustrate the invention in greater detail:

EXAMPLE 1

Pellets as a bath preparation for a medicinal bath against rheumatic complaints (pharmaceutical application)

2.5 kg of gelatin, 150 Bloom 1.0 kg of glycerol 6.5 kg of water 375 g of juniper berry oil (essential oil)

The gelatin is allowed to pre-swell in the glycerol/water mixture at room temperature for 30 minutes and is then dissolved at 60° C. After the essential oil of juniper berries has been added, the mixture is homogenized in an Ultra-Turrax, and the emulsion formed is added dropwise to liquid nitrogen at a temperature of −196° C. via the dosing device shown in FIG. 2. The pellets are dried in the air for 24 hours at 20° C. and filled into containers. 20 g of these pellets when added to a bath dissolve completely in the warm water, releasing the essential oil. This gives a medicinal bath against rheumatic complaints.

Also advantageous against muscular pain is a mixture of 10 g of these pellets and 10 g of oil of rosemary pellets prepared in the same manner.

Melissa oil can be used to prepare a sedative bath.

To prepare pellets for inhalation, Oleum Pini Pumilionis is employed, and the pellets are dissolved in hot water before inhalation.

EXAMPLE 2

Vitamin E emulsion pellets, freeze-dried for use in a protective cream (cosmetic use)

0.15 kg of vitamin E obtained from wheatgerm oil 1.0 kg of collagen hydrolysate, molecular weight 13,000–18,000 g/mol 9 kg of water The collagen hydrolysate is dissolved in water at room temperature, and the liquid vitamin E is added while homogenizing in an Ultra-Turrax. The resulting emulsion is added dropwise to liquid nitrogen at –196° C. via the dosing device as shown in FIG. 2 and shock-frosted in this manner. The water is then removed from the pellets by freeze-drying.

The dried pellets are incorporated into the following protective cream as "solid" vitamin E:

| Lipid phase: | |
| --- | --- |
| Tegomuls ® 90S | 2.5 kg |
| Soybean oil | 5.0 kg |
| Cocoa butter | 1.5 kg |
| Cetyl alcohol | 1.5 kg |
| Aqueous phase: | |
| Distilled water | 3.0 kg |
| Active substance: | |
| Vitamin E | 30 g | which correspond to 230 g of vitamin E emulsion pellets The pellets are emulsified with 1.8 l of water.

The components of the lipid phase are melted at 65° C., and mixed with 12 kg of the water, which has been heated to the same temperature, with stirring, until a homogeneous mixture has formed. After the cream has cooled to 30° C., the vitamin E/collagen hydrolysate emulsion is stirred in.

EXAMPLE 3

Echinacea pellets, unit doage form

| Original echinacea tincture | 2.16 kg |
| --- | --- |

Collagen hydrolysate, mean molecular weight 3000 g/mol 0.50 kg

| Distilled water | 0.50 kg |
| --- | --- |

The collagen hydrolysate is dissolved in water at room temperature and the solution is mixed with the original tincture. The ethanol is removed from the ethanol/water mixture at 40° C. under a vacuum of 5000 Pa (50 mbar) in a one-step vacuum evaporator.

The echinacea-containing solution is added dropwise to liquid nitrogen at –196° C. via a dosing device as shown in FIG. 2, giving the pellets. These pellets are subsequently subjected to freeze-drying with a primary drying step at –50° C. and 5 Pa (0.05 mbar) and a secondary drying step at 22° C.

After drying, the echinacea pellets have a diameter of 5 mm. 3×1 pellets taken everyday corresponds to the dosage as a prophylactic against common colds.

EXAMPLE 4

Echinacea soft gelatin pellets:

| Gelatin (140 Bloom) | 250 g |
| --- | --- |
| Glycerol | 100 g |

The gelatin is allowed to swell for 30 minutes in the mixture of fresh plant juice and glycerol, this mixture is heated to 40° C., and such an amount of water that the composition is still flowable is removed under a vacuum at 5000 Pa (50 mbar) in a one-step evaporator at 40° C. The composition is cryopelleted as in Example 1 via a dosing device as shown in FIG. 2 and the pellets are dried under the conditions indicated. The pellets, which have a diameter of 3.5 mm, are filled into a dosing dispenser. A unit dose of 5 pellets is withdrawn for use as a prophylactic.

EXAMPLE 5

Rutin suspension

| Gelatin 140 Bloom | 200 g |
| --- | --- |
| Glycerol | 150 g |
| Distilled water | 650 g |
| Rutin | 87.5 g |

A solution is prepared from gelatin, glycerol and water as described in Example 1, and the rutin is suspended in powder form. Pelleting and drying is effected as shown in Example 1. 5 pellets of diameter 3.5 mm contain a dose of 50 mg of rutin.

EXAMPLE 6

Aloe vera juice 150 g of collagen hydrolysate, mean molecular weight: 3000 g/mol 3000 g of Aloe vera juice, solids concentration 0.6% (w/w)

Freshly obtained fillets of Aloe vera leaves are homogenized, and the product is purified and filtered. The collagen hydrolysate is dissolved, with stirring, in the resulting, cooled Aloe vera juice. This solution is then used for forming pellets at –196° C. in an immersion bath containing liquid nitrogen, using the Cryopel$^R$ feeding device.

The shock-frosted, round shaped articles are dried in a freeze-drying plant where the primary drying step is carried out at –50° C. and 5 Pa (0.05 mbar) and the secondary drying step at 22° C.

This gives pellets of diameter 4 mm and an Aloe vera content of 10.7% (w/w, dry matter). Grading shows a granulometric accuracy of 78%.

The pellets dissolve completely in water at room temperature in the course of 20 seconds.

EXAMPLE 7

100 g of collagen hydrolysate, mean molecular weight: 3000 g/mol 50 g of mannitol 50 g of wheat protein hydrolysate, molecular weight<5000 g/mol 2000 g of Aloe vera juice, solids concentration 0.6%

The collagen hydrolysate, the wheat protein hydrolysate and the mannitol are dissolved in the cold Aloe vera juice, which has been processed as shown in Example 6, and pellets are prepared as shown in Example 6. This gives pellets of diameter 3 mm and an Aloe vera solids content of 5.7% (w/w). Dissolved in orange juice or passion fruit juice, these pellets can be used as a drink solution.

EXAMPLE 8

200 g of collagen hydrolysate, mean molecular weight: 3000 g/mol 4000 g of Aloe vera juice, 10×concentrate The Aloe vera juice obtained in Example 6 is brought to a concentration of 10× at 40° C. under a vacuum of 5000 Pa (50 mbar) by means of a one-step vacuum evaporator. The collagen hydrolysate is dissolved in the juice, and lyophilized pellets are prepared after short-term pasteurization. Round shaped articles of diameter 4.5 mm and an Aloe vera solids content of 54.5% (w/w) are obtained.

The pellets dissolve in water at room temperature in the course of 40 seconds.

5 g of these pellets dissolved in 100 ml of sterile water give an effective instant formula against solar dermatitis.

EXAMPLE 9

Incorporation of the pellets according to the invention into a night cream a) Preparation of the pellets 300 g of collagen hydrolysate, mean molecular weight: 13,000–18,000 g/mol 4000 g of Aloe vera juice, solids concentration 0.6%

Lyophilized pellets with an Aloe vera solids content of 7.4% (w/w) are prepared as described in Example 6.

b) Night cream formula

Lipid phase:
  200 g of Tegomuls 90S
  750 g of avocado oil

Aqueous phase:
  200 g of native collagen (3% solution, molecular weight 300,000 g/mol)
  30 g of elastin
  32 g of Aloe vera pellets as described under a)
  3000 g of freshly distilled water The lipid phase is melted at 70° C. The water is also heated to 70° C. and the elastin is dissolved therein. The resulting aqueous solution is homogenized in the lipid phase. The cream base is cooled to 35° C. The Aloe vera pellets are dissolved in the cold collagen solution and dispersed homogeneously in the cream base.

EXAMPLE 10

400 g of commercially available gelatin (170 Bloom)

300 g of glycerol (85%)

1300 g of Aloe vera juice, solids concentration 0.5% (w/w)

The gelatin powder is added to the freshly obtained and homogenized Aloe vera juice and allowed to pre-swell for approximately 45 minutes. The mixture is subsequently dissolved completely at 40° C. and the glycerol is admixed to give a homogeneous mixture.

The solution, which has a temperature of 40° C., is subsequently dosed into the immersion bath containing liquid nitrogen via the pump in the plant shown in FIG. 2, and pellets are made. The deep-frozen, round shaped articles are defrosted and dried at a rising temperature at between 25° C. and 40° C. The pellets have a residual moisture content of 10% and are storage-stable.

The pellets which have been prepared in this manner can be incorporated into a commercially available hydrogel (for example polyacrylate gel). The pellets swell in the hydrogel after 10 to 15 minutes up to twice their original size and form gel-like, readily meltable shaped articles which dissolve after application to the skin.

Alternatively, the pellets can also be added directly to the hydrogel without drying and without intermediate storage.

We claim:

1. A shaped article containing plant extract, which comprises a dispersion of the plant extract in a matrix composed predominantly of a skeleton builder of hydrophilic macromolecules selected from the group consisting of: collagen, gelatin, fractionated gelatin, collagen hydrolysates, gelatin derivatives, elastin hydrolysates, plant proteins, plant protein hydrolysates and mixtures thereof, wherein the shaped article contains 0.1 to 98% by weight of said plant extract.

2. A shaped article as claimed in claim 1, wherein the hydrophilic macromolecule comprises a thermoreversible sol/gel forming agent.

3. A shaped article as claimed in claim 2, wherein the sol/gel forming agent is a gelatin whose molecular weight distribution has a maximum of above $10^5$ D.

4. A shaped article as claimed in claim 1, wherein the matrix contains an additional skeleton builder from the group consisting of: albumins, agar-agar, gum arabic, pectins, tragacanth, xanthan, natural and modified starches, dextrans, dextrins, maltodextrin, chitosan, alginates, cellulose derivatives, dextran, sugars, glycine, lactose, sorbitol, mannitol or polyvinylpyrrolidone.

5. A shaped article as claimed in claim 4, wherein the matrix contains less than 50% by weight of additional skeleton builder.

6. A shaped article as claimed in claim 1, which further comprises a pharmaceutically acceptable auxiliary or carrier for the matrix.

7. A shaped article as claimed in claim 1, which contains 0.1–60% by weight of plant extract.

8. A shaped article as claimed in claim 1, wherein the plant extract is selected from the group consisting of:
  solid plant extracts, liquid plant extracts, hydrophilic plant extracts, lipophilic plant extracts, individual plant constituents and mixtures thereof.

9. A shaped article as claimed in claim 1, wherein the plant extract is Aloe vera juice.

10. A shaped article as claimed in claim 1, in the form of a lyophilisate.

11. A shaped article as claimed in claim 1, which is rapidly dissolving and wherein the matrix is composed of essentially a plant protein, plant protein hydrolysate, collagen hydrolysate, a gelatin derivative which is soluble in cold water, or gelatin whose molecular weight distribution has a maximum of below $10^5$ D.

12. A shaped article as claimed in claim 1, further comprising (1) a plasticizer selected from glycerol and sorbitol and (2) masking flavors wherein the plasticizer and masking flavors comprise 1–50% by weight of the shaped article.

13. A shaped article as claimed in claim 12, in solid, semi-solid or gel-like form.

14. A shaped article as claimed in claim 13, in the form of a pellet.

15. A shaped article containing Aloe vera juice, which comprises a dispersion of the Aloe vera juice in a matrix predominantly composed of skeleton builders of hydrophilic macromolecules selected from the group consisting of: collagen, gelatin, fractionated gelatin, collagen hydrolysates, gelatin derivatives, plant proteins, plant protein hydrolysates, elastin hydrolysates and their mixtures, wherein said shaped article contains 0.1 to 98% by weight of said Aloe vera juice.

16. A process for the preparation of shaped articles containing plant extract, wherein
   a) a skeleton builder of hydrophilic macromolecules selected from the group consisting of: collagen, gelatin, fractionated gelatin, collagen hydrolysates, gelatin derivatives, plant proteins, plant protein hydrolysates, elastin hydrolysates and mixtures thereof, is mixed with plant extracts selected from the group consisting of: hydrophilic liquid plant extracts, aqueous extracts, alcoholic extracts, and mixtures thereof to produce a mixture that comprises a dispersion of the plant extract in a matrix of said skeleton builder; and
   b) the resulting mixture of skeleton builder and plant extract is added dropwise to an intensely cold inert liquefied gas, thus making it into shaped articles, wherein the mixture is added at a temperature and pressure effective to form drops of said mixture and wherein each of said shaped articles contains 0.1 to 98% by weight of said plant extract.

17. A process as claimed in claim 16, wherein the skeleton builder comprises a sol/gel forming agent.

18. A process as claimed in claim 16, wherein the shaped article prepared is a pellet.

19. A process as claimed in claim 18, wherein the pellets are freeze-dried.

20. A process as claimed in claim 16, wherein the plant extract employed is Aloe vera juice.

21. A process as claimed in claim 20 wherein the resulting mixture obtained in step b) is added dropwise into a bath having a temperature of −108° C. to −210° C.

22. A process as claimed in claim 16, wherein step b) produces pellets that are thereafter incorporated into a cream or hydrogel base.

23. A process as claimed in claim 16, wherein step a) comprises preparing a solution of the skeleton builder and mixing the hydrophilic liquid plant extract into said solution.

24. A process as claimed in claim 16, wherein the plant extracts comprise alcoholic extracts said process further comprising the step of removing alcohols from the mixture formed in step a).

25. A process as claimed in claim 16, wherein step a) comprises concentrating the mixture formed.

26. A process as claimed in claim 16, wherein a lipophilic extract is emulsified in the matrix, or a solid plant extract is suspended or dissolved in the matrix in step a).

27. A process as claimed in claim 16, wherein step b) comprises adding the resulting mixture into liquid nitrogen.

28. A process as claimed in claim 16, wherein an additional skeleton builder from the group consisting of: albumin, agar-agar, gum arabic, pectins, tragacanth, xanthan, natural and modified starches, dextrans, dextrins, maltodextrin, chitosan, alginates, cellulose derivatives, dextran, sugars, glycine, lactose, mannitol or polyvinylpyrrolidone is added to the dispersion of skeleton builder and plant extract.

29. A process as claimed in claim 18 wherein the resulting mixture obtained in step b) is added dropwise into a bath having a temperature of −108° C. to −210° C.

30. A process as claimed in claim 16, wherein the mixture produced in step a) further comprises a plasticizer selected from glycerol, sorbitol and mixtures thereof wherein the plasticizer comprises 1–50% by weight of said mixture.

31. A process as claimed in claim 16, wherein gelatin whose molecular weight distribution has a maximum of above $10^5$ D is mixed with the plant extract at not more than 60° C. to act as skeleton builder.

32. A process as claimed in claim 31, wherein step a) comprises mixing liquid Aloe vera juice with gelatin at not more than 40° C.

33. A process as claimed in claim 16 further comprising the step of drying the shaped articles produced in step b) at not more than 50° C.

34. A process as claimed in claim 16 wherein the resulting mixture obtained in step b) is added dropwise into a bath having a temperature of −108° C. to −210° C.

35. A pharmaceutical dosage form containing a shaped article containing plant extract, which comprises a dispersion of the plant extract in a matrix composed predominantly of a skeleton builder of hydrophilic macromolecules selected from the group consisting of: collagen, gelatin, fractionated gelatin, collagen hydrolysates, gelatin derivatives, elastin hydrolysates, plant proteins, plant protein hydrolysates and mixtures thereof, wherein the shaped article contains 0.1 to 98% by weight of said plant extract.

36. A food preparation containing a shaped article containing plant extract, which comprises a dispersion of the plant extract in a matrix composed predominantly of a skeleton builder of hydrophilic macromolecules selected from the group consisting of: collagen, gelatin, fractionated gelatin, collagen hydrolysates, gelatin derivatives, elastin hydrolysates, plant proteins, plant protein hydrolysates and mixtures thereof, wherein the shaped article contains 0.1 to 98% by weight of said plant extract.

37. A cosmetic product containing a shaped article containing plant extract, which comprises a dispersion of the plant extract in a matrix composed predominantly of a skeleton builder of hydrophilic macromolecules selected from the group consisting of: collagen, gelatin, fractionated gelatin, collagen hydrolysates, gelatin derivatives, elastin hydrolysates, plant proteins, plant protein hydrolysates and mixtures thereof, wherein the shaped article contains 0.1 to 98% by weight of said plant extract.

* * * * *